(12) United States Patent
Carmi

(10) Patent No.: US 11,030,748 B2
(45) Date of Patent: Jun. 8, 2021

(54) AUTOMATIC CT DETECTION AND VISUALIZATION OF ACTIVE BLEEDING AND BLOOD EXTRAVASATION

(71) Applicant: KONINKLIJKE PHILIPS N.V., Eindhoven (NL)

(72) Inventor: Raz Carmi, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 107 days.

(21) Appl. No.: 16/340,421

(22) PCT Filed: Oct. 19, 2017

(86) PCT No.: PCT/EP2017/076658
§ 371 (c)(1),
(2) Date: Apr. 9, 2019

(87) PCT Pub. No.: WO2018/077707
PCT Pub. Date: May 3, 2018

(65) Prior Publication Data
US 2020/0051246 A1    Feb. 13, 2020

(30) Foreign Application Priority Data
Oct. 28, 2016  (EP) .................................... 16196368

(51) Int. Cl.
*G06T 7/00* (2017.01)
*A61B 5/02* (2006.01)
(Continued)

(52) U.S. Cl.
CPC ........ *G06T 7/0016* (2013.01); *A61B 5/02042* (2013.01); *A61B 5/055* (2013.01);
(Continued)

(58) Field of Classification Search
CPC ..... G06T 7/0016; G06T 5/50; A61B 5/02042; A61B 5/055; A61B 6/032; A61B 6/037; A61B 6/481; A61B 8/481
See application file for complete search history.

(56) References Cited

U.S. PATENT DOCUMENTS 7,939,093 B2    5/2011   John
8,150,126 B2 *  4/2012   Chen ....................... G06T 5/002
                                                 382/130
(Continued)

FOREIGN PATENT DOCUMENTS

| WO | 2007016442 | 2/2007 |
| WO | 2011125369 | 10/2011 |
| WO | 2014036638 | 3/2014 |

OTHER PUBLICATIONS

Martinez-Costa, et al: "Macular Edema Computer-Aided Evaluation in Ocular Vein Occlusions", Computers and Biomedical Research, Academic Press, London, GB, vol. 31, No. 5, May 25, 2002.
(Continued)

*Primary Examiner* — Santiago Garcia
(74) *Attorney, Agent, or Firm* — Larry Liberchuk

(57) ABSTRACT

An image processing system (IPS) and related method. The system comprises an input interface (IN) for receiving an earlier input image (Va) and a later input image (Vb) acquired of an object (OB) whilst a fluid is present within the object (OB). A differentiator (Δ) is configured to form a difference image (Vd) from the at least two input images (Va,Vb). An image structure identifier (ID) is operable to identify one or more locations in the difference image. Based on a respective feature descriptor that describes a respective neighborhood around said one or more locations. An output interface (OUT) outputs a feature map (Vm) that includes the one or more locations.

13 Claims, 4 Drawing Sheets

(51) Int. Cl.
*A61B 5/055* (2006.01)
*A61B 6/00* (2006.01)
*A61B 8/08* (2006.01)
*G06T 5/50* (2006.01)
*G06T 11/00* (2006.01)
*A61B 6/03* (2006.01)

(52) U.S. Cl.
CPC .............. *A61B 6/032* (2013.01); *A61B 6/037* (2013.01); *A61B 6/481* (2013.01); *A61B 8/481* (2013.01); *G06T 5/50* (2013.01); *G06T 11/001* (2013.01); *G06T 2207/10081* (2013.01); *G06T 2207/20221* (2013.01); *G06T 2207/20224* (2013.01); *G06T 2207/30101* (2013.01); *G06T 2207/30196* (2013.01)

(56) References Cited

U.S. PATENT DOCUMENTS

| | | | |
|---|---|---|---|
| 9,092,691 B1 | 7/2015 | Beaumont | |
| 2004/0215081 A1* | 10/2004 | Crane | A61B 5/0059 600/473 |
| 2005/0111718 A1 | 5/2005 | MacMahon | |
| 2006/0173360 A1* | 8/2006 | Kalafut | A61B 5/0059 600/478 |
| 2011/0081057 A1 | 4/2011 | Zeng | |
| 2012/0157774 A1* | 6/2012 | Kaku | A61B 1/0005 600/178 |
| 2015/0356734 A1 | 12/2015 | Ooga | |
| 2016/0015348 A1* | 1/2016 | Ohishi | A61B 6/5217 600/431 |
| 2016/0300359 A1 | 10/2016 | Lachner | |
| 2017/0258736 A1* | 9/2017 | Elbaz | A61K 9/5138 |
| 2017/0285125 A1* | 10/2017 | Daniel | G01R 33/56509 |
| 2018/0078232 A1* | 3/2018 | Silbert | G16H 50/30 |
| 2018/0153617 A1* | 6/2018 | Dupuy | A61B 5/055 |
| 2018/0249925 A1* | 9/2018 | Ellingson | A61B 5/0042 |

OTHER PUBLICATIONS

Momeni et al: "An automatic aneurysm extraction algorithm in fused brain digital subtraction angiography images", Biocybernetics and Biomedical Engineering, vol. 35, No. 4, Jan. 1, 2015.

Hamilton, et al: "Multi-detector CT Evaluation of Active Extravasation in Blunt Abdominal and Pelvic Trauma Patients", RadioGraphics, October issue 28(6), pp. 1603-1616, (2008).

Lowe et al: "Distinctive Image Features from Scale-Invariant Keypoints", International journal of Computer Vision, vol. 60, Issue 2, 2004, pp. 91-110.

Uyeda et al: "Active Hemorrhage and Vascular Injuries in Splenic Trauma: Utility of the Arterial Phase in Multidetector CT", Radiology, 2014.

Suzuki et al: "Active Bleeding in Acute Subarachnoid Hemorrhage Observed by Multiphase Dynamic-Enhanced CT", Am J Neuroradiol, (2012).

Huprich et al: "Obscure Gastrointestinal Bleeding: Evaluation with 64-Section Multiphase CT Enterography—Initial Experience", Radiology (2008).

Gomez et al: "Gastrointestinal bleeding: The role of radiology", Radiología (2011).

Huprich et al: "Multiphase CT Enterography Evaluation of Small-Bowel Vascular Lesions", AJR (2013).

Badillo et al: "Low Acute Gastrointestinal Bleeding: 40-Multidetector Row Helical CT as a first line diagnostic procedure", 2009.

* cited by examiner

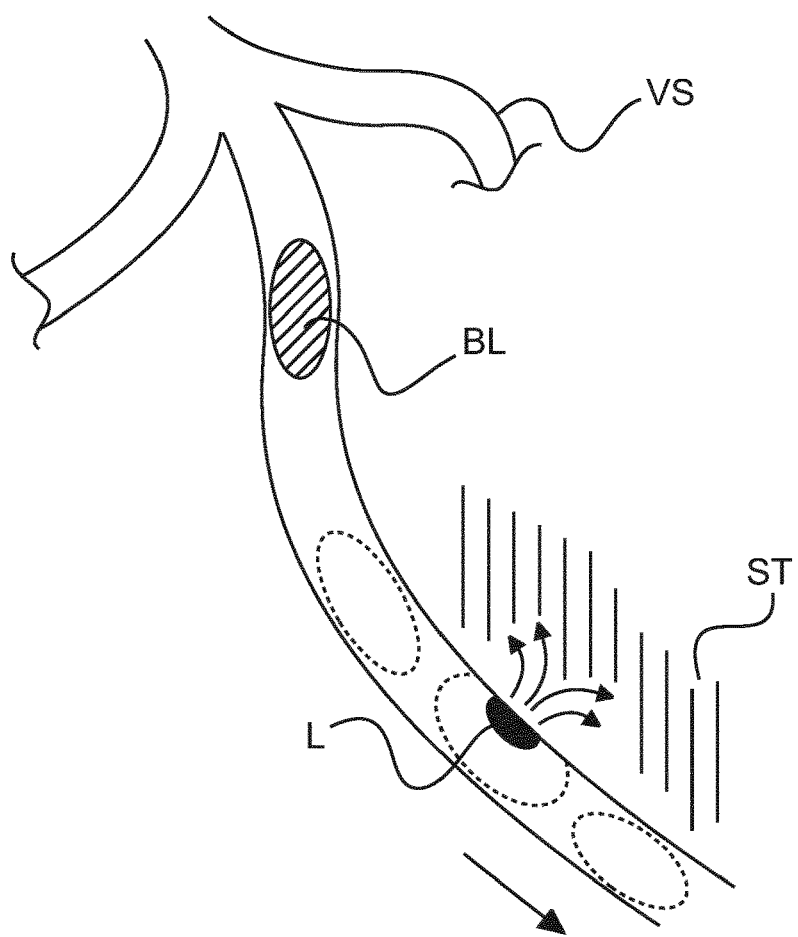
Fig. 2
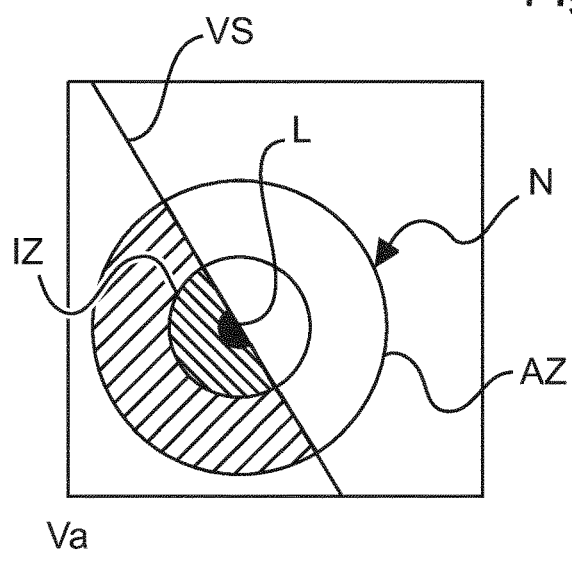 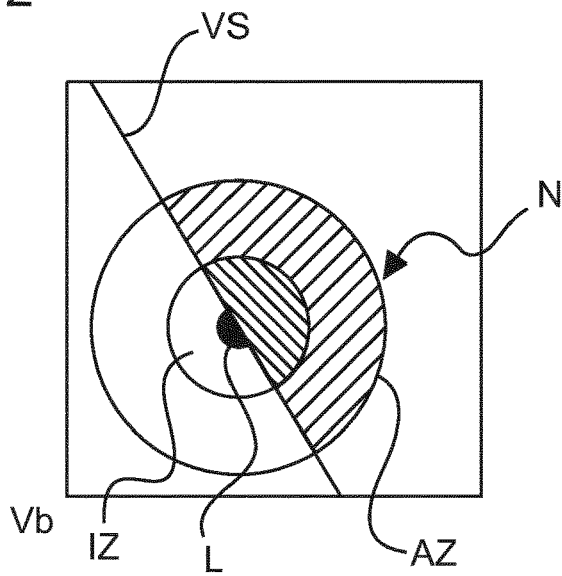
ta < tb
Fig. 2A    Fig. 2B

AUTOMATIC CT DETECTION AND VISUALIZATION OF ACTIVE BLEEDING AND BLOOD EXTRAVASATION

CROSS REFERENCE TO RELATED APPLICATIONS

This application is the U.S. National Phase application under 35 U.S.C. § 371 of International Application No. PCT/EP2017/076658 filed Oct. 19, 2017, published as WO 2018/077707 on May 3, 2018, which claims the benefit of European Patent Application Number 16196368.1 filed Oct. 28, 2016. These applications are hereby incorporated by reference herein.

FIELD OF THE INVENTION

The invention relates to an image processing system, to a method of image processing, to a computer program element, and to a computer readable medium.

BACKGROUND OF THE INVENTION

As reported by J D Hamilton et al in "Multi-detector CT Evaluation of Active Extravasation in Blunt Abdominal and Pelvic Trauma Patients", RadioGraphics, October issue 28(6), pp 1603-1616, (2008), " . . . Improvements in the technology of computed tomography (CT) and emergency medical services have expedited the work-up and triage of the traumatized patient . . . ". Being able to quickly localize a bleeding source can improve patient management. Active extravasation is an important indicator for morbidity and mortality in poly-trauma patients because it is an indicator for significant vessel or organ injury.

J D Hamilton further reports that "active extravasation refers to administered contrast agent that has escaped from injured arteries, veins, bowel, or urinary tract. Active extravasation is seen in part of trauma patients in whom CT reveals a hematoma in the abdomen or pelvis".

It is recognized that a dual phase CT protocol is better suited to detect extravasation than single phase CT. The way in which an extravasation occurrence presents itself in such imagery is as a "jet or focal area of hyper-attenuation within a hematoma on initial images that fades into an enlarged, enhanced hematoma on delayed images". This finding indicates significant bleeding and must be quickly communicated to a clinician, since potentially life-saving surgical or endovascular repair may be necessary. In short, time is of essence.

Other than in trauma cases, active bleedings may also occur in several other acute diseases or conditions such as brain vascular abnormalities or gastrointestinal diseases. Potential organs found to be inflicted by internal bleedings are the brain, spleen, general abdomen region, liver, kidneys, small bowel, colon, and regions near bone fractures.

In the clinical routine of such cases, the user (physician, clinician, etc) is usually required to look simultaneously on two (or three or more) CT phase images and to then intuitively guess whether there is indeed any bleeding or similar leakage event. This must often be done in a stress situation. Furthermore, correct interpretation of internal imagery (such as X-ray or CT) is often difficult and requires a lot of prior training and experience.

The research article "An automatic aneurysm extraction algorithm in fused brain digital subtraction angiography images" by Saba Momeni and Hossein Pourghassem, Biocybernetics and Biomedical Engineering, vol. 35, issue 4, pp. 264-275, 2015, describes an algorithm for automatic aneurysm extraction using digital subtraction angiography (DSA) images. The algorithm firstly removes vessel structures. Then, aneurysms can be extracted by applying circular Hough transform and region growing algorithms.

US 2011/0081057 A1 describes a real-time quantitative coronary angiography (QCA) system for automatic stenosis estimation in DSA images. The stenosis can be detected based on a two-step procedure. The first step is to segment vessels in the region of interest, and then the second step is applied to estimate the stenosis by measuring the width variation of the segmented vessels.

US 2016/0300359 A1 addresses a data processing method for determining an enhancing structure of interest within an anatomical body part. The enhancing structure of interest may be a tumor or metastasis, which accumulates a contrast agent. The enhancing structure of interest is determined based on two magnetic resonance imaging scans, one scan without contrast agent and another scan with contrast agent.

US 2005/0111718 A1 addresses a method for performing computer aided diagnosis on temporal subtraction images of objects. The temporal subtraction image is interpreted to identify and indicate the locations of regions representing pathologic change. Regions with indications of pathologic change are then super-imposed as a computer aided detection output onto the temporal subtraction image or on the original image.

SUMMARY OF THE INVENTION

There may therefore be a need for an image-based system and method to support a user in identifying internal leakage occurrences.

The object of the present invention is solved by the subject matter of the independent claims where further embodiments are incorporated in the dependent claims. It should be noted that the following described aspect of the invention equally applies to the method of image processing, to the computer program element and to the computer readable medium.

According to a first aspect of the invention there is provided an image processing system, comprising:

an input interface for receiving an earlier input image and a later input image acquired of an object whilst a fluid is present within the object;

a differentiator configured to form a difference image from the at least two input images;

an image structure identifier operable to identify one or more locations in the difference image, based on a respective feature descriptor that describes a respective neighborhood around said one or more locations; and an output interface for outputting a feature map that includes the one or more locations.

'According to one embodiment the forming by the differentiator of image values of the difference image includes taking differences to obtain difference image values and increasing or decreasing said difference image values based on one or more pre-set intensity thresholds to obtain adjusted difference image values.

According to one embodiment, said feature descriptor is computed by the identifier to describe an intensity distribution in said neighborhood.

According to one embodiment said intensity distribution represents adjacent regions with, respectively, positive and negative image values. The distribution can be said to have a "signature plateau". This type of distributions of positive and negative image values in the difference image have been found to indicate leakage events.

According to one embodiment the intensity distribution is indicative of fluid escaping through a leak in a conduit within the object.

According to one embodiment the identifier is configured to compute the feature descriptor based on a wavelet analysis of the difference image.

According to one embodiment the wavelet analysis is applied along different spatial directions. In one embodiment, Haar wavelets are used but other Daubechies wavelets or but wavelets of other types are also envisaged herein. The preferred scale and direction of the wavelets are effectively determined in 3D, eg by analyzing all three orthogonal views.

According to one embodiment, the one or more locations of interest are identified from among a collection of candidate locations computed by a feature detector applied to the difference image, in particular in a scale space representation of the difference image.

Preferably, the detector (such as a blob detector) and the feature descriptor is used in the context of a "Feature-based interest-points detector and descriptor analysis" algorithm (referred to herein as image processing algorithms of the "DD type"), such as SURF, SWIFT or derivatives thereof.

According to one embodiment the system comprises a visualizer configured to render on a display unit a visualization of said feature map in spatial association with at least one of the input images or with another image of the object.

According to one embodiment the visualization includes a representation of the respective neighborhood, said representation being color- or grey value coded based on a strength of the respective feature descriptor or on a strength of a response of the feature detector.

According to one embodiment, said object is a human or animal anatomy and said liquid is blood and the conduit being a blood vessel. In other embodiments, the liquid is any other body fluid that escapes from its natural anatomic conduit (organ, etc). According to one embodiment, at least one of the input images is any one of: a CT image, an MRI image, a US image, a PET or a SPECT images.

The proposed system provides an automatic tool that operates to indicate to the user regions within the object ("object" as used herein may also refer to human an animal patients) possible leakage occurrences, such as internal bleeding in organs of a patent. The proposed system can help significantly improve and speed-up clinical workflow.

In short and according to one embodiment, the proposed system is configured for (preferably) automatic CT detection and visualization of active bleeding and blood extravasation. By analyzing dual-phase contrast-enhanced CT as the input data, an algorithm of the DD type applies feature-based interest-points detector and descriptor analysis to quantify significance characteristics and locations of relevant points in the volume.

Based on these localizations, a feature map is used for visualization to enable an improved clinical diagnostics workflow. In particular, the localization algorithm is configured to detect typical patterns of active extravasation at dual phase CT, for example, the earlier mentioned jet or focal area of hyper-attenuation within a hematoma recorded in an earlier image (acquired in the dual phase protocol) that then fades into an enlarged, enhanced hematoma recorded in a delayed image.

According to another aspect there is provided a method of image processing, comprising the steps of:

receiving an earlier input image and a later input image acquired of an object whilst a fluid is present within the object forming a difference image from the at least two input images;

identifying one or more locations in the difference image, based on a respective feature descriptor that describes a respective neighborhood around said one or more locations; and outputting a feature map that includes the one or more locations.

According to one embodiment the method comprises visualizing the feature map on a display device.

According to another aspect there is provided a computer program element which, when being executed by a processing unit is adapted to perform the method.

According to yet another aspect there is provided a computer readable medium having stored thereon the program element.

Although the main application of the proposed system and method is in the medical field for processing imagery supplied by medical imaging modalities, applications in other fields are not excluded herein. For instance, the proposed system and method may equally be put to good use in examining imagery of inaccessible plumbing systems or geological examination of cave systems or drilling sites such as for oil, fracking etc, where the relevant liquid (water, oil) may leak from pipes or other equipment into masonry, surrounding soil, aquifer, strata, etc. Here too, the proposed system may further the objective of being able to quickly establish whether or not there is a leakage situation in order to then take remedial action, if necessary.

BRIEF DESCRIPTION OF THE DRAWINGS

Exemplary embodiments of the invention will now be described with reference to the following drawings (which are not necessarily to scale), wherein:

FIG. 2 shows a schematic representation of a leakage situation;

DETAILED DESCRIPTION OF EMBODIMENTS

Figure 1:
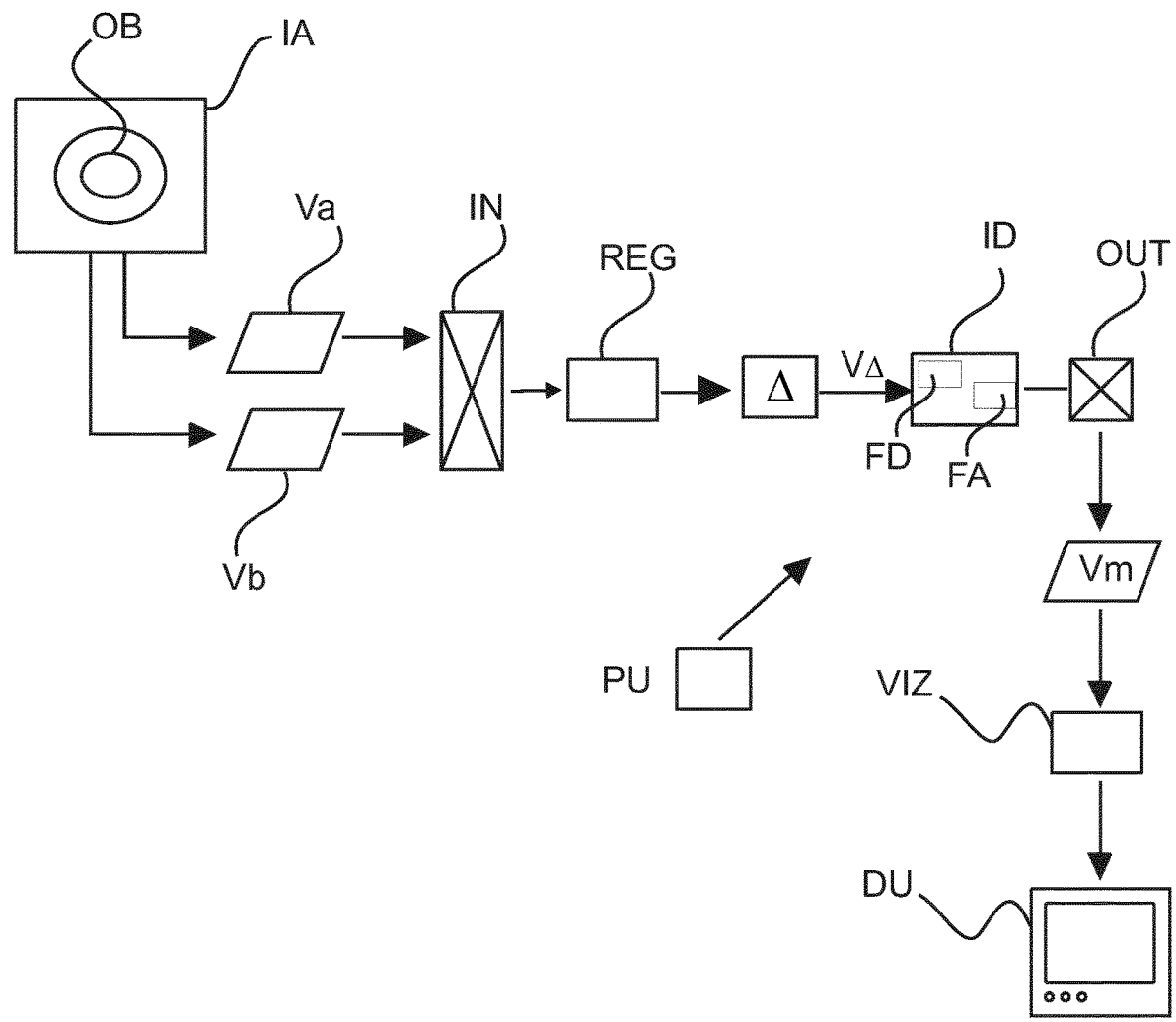
FIG. 1 shows a block diagram of an image processing system.

With reference to FIG. 1 there is shown a schematic block diagram of an image processing system IPS as proposed herein.

The system IPS is implemented by one or more data processing devices PU. The system is configured to process digital imagery of an object to make it easier to localize one or more instances of internal leakage inside the object. The term "object" is used herein in a general sense to include inanimate objects or animate objects (such as a human or animal patient or a specific anatomy thereof). The main field of application of the proposed image processing system is in the medical field where there is an interest to quickly localize occurrences of internal bleedings or other extravasations in a human or animal patient. Reliably and quickly localizing such internal bleedings is critical for instance in multi-trauma patients where prompt remedial action is called for.

The imagery on which operation of the image processing system is based is supplied by a suitable imaging apparatus IA that operates to image the object OB. We shall refer in the following to the object OB as the patient with the understanding that applications other than in the medical field are also envisaged herein.

The imaging apparatus IA is configured to acquire imagery of the internals of the patient. The acquired imagery is such that it is capable of conferring image contrast to the liquid of interest (such as blood) involved in the leakage. For instance, in internal bleedings (which are of main interest herein), blood escapes through a leakage point in a vessel (caused by rupture, bursting etc) into surrounding tissue. The imaging technology implemented by the imaging apparatus IA is either such that it is natively capable of providing such liquid contrast or additional measures need to be taken to ensure that it does. For instance, X-ray imaging as such is usually not able to provide contrast sufficient to localize blood in the image. But this can still be achieved if a contrast agent is introduced prior to the imaging to the patient by injection into a suitable blood vessel. A certain quantity of this contrast agent (sometimes referred to as a "bolus") is administered. The bolus then travels with the blood flow and passes through vessels and past the anatomies of interest whilst images are acquired. An example of an imaging technology that is capable of natively recording liquid contrast is MRI (magnetic resonance imaging) or X-ray based phase contrast imaging which is specifically included herein. This later image technology uses an interferometer arranged in the X-ray beam of the X-ray imaging apparatus to reveal excellent soft tissue and even blood contrast. Apart from X-ray imaging modalities (2D radiography or CT (computed tomography)), which are the main focus herein, other imaging modalities are not excluded such as US (ultrasound) or functional imaging such as SPECT (Single-photon emission computed tomography) or PET (Positron emission tomography), or others.

The input imagery on which operation of the proposed system is based can be two dimensional (2D) or three dimensional (3D). The imagery comprises a two or three dimensional array of numerical data. The numerical image data is referred to herein as image values. Each image value is addressable by its image coordinates (x,y) or (x,y,z). Each image coordinate corresponds to a location in the patient. The image values encode or correspond to a physical quantity of interest depending on the imaging modality used. For instance, in X-ray imaging, such as in CT imaging, the image values may expressed in Hounsfield units which quantify the amount of absorption that the X-ray beam has suffered in its passage through the patient tissue, relative to the absorption through water. In X-ray imaging (not only in CT), the image values are commonly referred to as intensities. In other imaging modalities the image values may represent different quantities. For instance, in US, the image values represent re-bouncing echoes of ultrasound.

The imaging values that make up the imagery can be fed into a graphical visualizer component VIZ which then maps the image values to a suitable grey or color palette and this is then used by graphics processing components of the system to render the image for view on a display unit DU. The display unit DU may be a mounted monitor in an operation theatre. In other embodiments, the display unit is in a mobile device such as a laptop, tablet or smart phone or other. Preferably, the input imagery is acquired in a dual-phase mode. In other words, the input imagery comprises two or more images acquired at different points in time to better capture the dynamics of the blood flow. The imagery in particular includes an earlier (or first phase) image and a later (or second phase) image, the two (or more) images acquired at a suitably chosen time delay.

Operation of the proposed image processing system IPS is based on a class of image processing algorithms sometimes referred to as feature-based detector and descriptor analyzers. We shall refer to this type of image processing algorithms in the following as "DD (detector and descriptor) algorithms" or "algorithms of the DD type". The operation of DD type algorithms can broadly be described as a two-step approach: there is, first, a detection step and, second, a feature descriptor extraction step. In the first step, a detection technique (eg. blob detector) is used to detect a collection of locations (referred to herein as "candidate locations" or "candidate points") that are of potential interest. Image neighborhoods (eg, n-dimensional-rectangles or n-dimensional spheres, $n \geq 2$) of the so collected candidate locations in the image are then analyzed in the second (feature extraction) step. In this analysis, feature descriptors are constructed that capture image structures of interest, such as particular image value distributions. The feature descriptors are preferably quantifiable in a suitable magnitude (or "strength") which is preferably invariant under rotation and/or scale. The proposed image processing system, based on these feature descriptors, selects from the (initial) collection of candidate points a sub-set of locations of interest (LI). These locations along with their feature descriptors of their respective neighborhoods are then output as locations indicative of leakage occurrence. The LIs can be output in list form but are preferably rendered graphically combined into the input imagery or into imagery derived from the input imagery. The feature descriptors of the respective neighborhoods of the LIs can be used optionally for a visual mark-up of the likelihood or probability for leakage.

Bleeding (or any extravasation other than blood, such as urine, lymph or other body fluids) that occurs inside the human or animal anatomy can be broadly categorized as a leak point in a system of conduits (such as the blood vessels) shielded from direct visual inspection. Before providing more details of the operation of the proposed image processing system, we make reference to FIG. 2 where a schematic representation is shown of a leak situation in a system of conduits, such as in a blood vessel in the human or animal anatomy. Suppose a pair of dual phase X-ray imagery has been acquired of a patient after injection of a suitable amount of contrast agent CA. The bolus BL travels with blood flow through the vessel system VS until it passes leak L. A leak L can then be thought of as vessel VS's integrity being compromised (by rupture, tear or other) at leak point L. Some blood entrained with CA escapes into surrounding tissue ST through leakage point L and is absorbed there while some other part of the CA continues to travel within the vessel VS past the leakage point L.

In yet more detail and referring now to inset FIGS. 2A, 2B, these show close-ups of two dual-phase images, Va (left) and Vb (right) acquired in the dual phase imaging protocol whilst bolus BL passes leak point L. The first phase image Va has been acquired earlier, at time ta, than the later, second phase, image Vb that has been acquired at time tb. In other words, we have, of the same anatomy at the leakage point L, two images, an earlier one and a later image.

Suppose we define a neighborhood N, say a circle, around leak point L. Let us further define within said neighborhood N an inner zone IZ proximal to leak occurrence L and, more distal to leak L, an outer zone AZ around the inner zone IZ. The outer zone AZ does not necessarily surround the inner IZ completely as shown in FIGS. 2A,B although the case of a completely surrounding other zone AZ is also envisaged herein. Now, having in mind the limited quantity of CA available that flows past the leak L with some of the CA entrained blood escaping through L, we may observe the following "morphology" or image pattern at said neighborhood N and across the two images Va, Vb if the delay (tb−ta) is suitably timed: a localized contrast enhancement at IZ in the early phase Va is reduced on the subsequent delayed phase Vb, and in addition, in the adjacent, extended, peripheral area AZ there is increased contrast-enhancement in the delayed phase Vb, relative to the early phase Va contrast enhancement in IZ.

In this situation, If we form a difference image $V_\Delta$ based on the two images Va,Vb, we observe for the two zones IZ, AZ of neighborhood N a "sign trading" effect, which may be described by the following five properties:

i) region IZ with negative values is adjacent to a region AZ with positive values.

ii) region IZ with negative values is smaller than the adjacent region AZ with positive values.

iii) region AZ with positive values tends to surround (not necessarily completely) the region with negative values.

iv) the negative values, of the said corresponding region, have relatively large absolute values.

v) the positive values, of the said corresponding region, have relatively large absolute values.

In the above properties i)-v), it is assumed that the first phase Va image is subtracted from the second phase image Vb. It will be understood that equivalent properties are obtained instead, when one subtracts the second phase image Vb from the first phase image Va. In this later case, the equivalent five properties are obtained by exchanging the qualifiers "negative" and "positive" in i)-v) above. In properties iv, v), the relative magnitudes are taken relative to suitably chosen value thresholds or value ranges with value clipping. If the images are in scale space representation (on which more below) spatial scale ranges are also considered in defining the magnitudes.

If we encode the two signs (+,−) with a black-and-white palette, the neighborhood N having the sign trading property may be visualized as a localized "doughnut" shape image structure in the difference image, with (depending on the coding order), a small "black" disk surrounded (not necessarily completely) by a wide "white" ring.

If at least one of the properties ((eg, i) or any of ii-v)) is fulfilled, we may say that a given neighborhood N in the difference image has the "sign(ature) trading property". The sign trading property can hence be used as an indicator for a particular sign (+ and −) distribution of (difference) image values in the given neighborhood in the difference image. Not all properties are necessarily always fulfilled, although this is preferred. All combinations of finite sub-set selections from among the properties i)-v) are envisaged herein for different embodiments. In particular embodiments are envisaged where only a single property (eg, only property i)) is fulfilled or only exactly two properties are fulfilled, etc. Preferably however, as said earlier, all properties are fulfilled.

The above described sign trading property in dual phase difference imagery has been found to be an indicator for leakage occurrences. The image processing system as proposed herein includes a filter component ID configured to respond to locations ILs in the difference image with neighborhoods having the sign trading property. More particularly, it has been found by Applicant that DD type algorithms can be adjusted to respond particularly well to locations with sign trading in their respective neighborhoods. As will be appreciated from above explanations in relation to FIG. 2, there is a large variety in imaging morphology that may exhibit sign trading like patterns. The proposed DD algorithm based system IPS hence avoids model-based segmentation techniques to so achieve a much more robust performance in correctly identifying sign trading locations (and hence leakage instants) in dual phase difference imagery as supplied by any suitable imaging modality.

It should be understood that the proposed identification of leakage points is not immune to "false positives". In certain natural flow events in the anatomy such as in the liver a similar intensity pattern may be detected although there is no actual bleeding event. Blood vessels in the liver are supplied by arterial contrast enhancement, whilst the surrounding liver parenchyma is not yet supplied with hepatic portal blood. Then, in the later portal phase, the enhancement in the arterial vessels starts to washout, but at that time, the liver parenchyma is contrast-enhanced by the hepatic portal supply. Therefore the proposed leakage identification algorithm or system IPS is best used in combination with medical knowledge to exclude regions that are known to "mimic" leakage such as the liver. Even though the proposed system has been found to produce on occasion such false positives, it can still help the user to more quickly examine X-ray imagery for bleeding events. The LIs as returned by the system IPS may be understood as suggestions for locations that would "warrant closer inspection" and in that sense the system supports a quicker orientation in an otherwise unstructured (medical) input image. This may be helpful in particular in situations where the user is under great mental stress as is often the case in emergency rooms in ever busy (in particular urban) clinical environments.

Referring now back to the block diagram in FIG. 1, operation of the proposed processing system IPS is broadly as follows. At least two dual phase images of the object, Va, Vb are received at input port IM. The two images Va, Vb have been acquired by the imaging apparatus (eg, CT) at two different times, ta,tb separated by a suitably chosen delay time (tb−ta). This can be achieved when operating the X-ray imaging apparatus IA (or any other modality) according to a dual phase protocol.

Based on the two (or more) input images, Va,b, a differentiator $\Delta$ forms the difference image $V\Delta$. In particular, either the earlier image Va is subtracted pixel/voxel-wise from the later image Vb or the later image is subtracted pixel/voxel-wise from the earlier image. Preferably operation of the differentiator does not merely amount to the taking of arithmetic differences to form difference image values but also includes a non-linear processing of said difference values by thresholding and clipping as will be explained in more detail below at FIG. 3. This clipping or thresholding against a set of pre-defined thresholds is a non-linear operation that allows to emphasize or to mitigate certain effects of the agent contrast distribution during the earlier and later phases.

Optionally, prior to taking the difference image there is a registration unit REG that registers the two images onto each other. Further, optionally, in combination or instead of the foregoing, spectral iodine density volumetric maps of the two volumes can be used to assist the differentiator. These maps may be obtained from spectral CT data.

Preferably, the X-ray imaging apparatus IA is a CT X-ray imager and the input images Va, Vb are 3D image volumes. The image volumes are obtained by reconstructing cross sectional imagery of the object from rotational projection imagery. Suitable reconstruction algorithms include filtered-backward projection and others. In other words, each image volume Va, Vb (acquired at different times) is formed from a respective stack of cross sectional images with co-ordinates x,y and z along the scan axis z. In the following we will refer chiefly to CT images with (x,y,z)-coordinates, although the described system and method can also be applied to purely 2D imagery (with coordinates x,y).

Once the difference image $V_A$ is formed, either as a mere arithmetic difference image or as non-linearly processed difference image (eg, by clipping or thresholding), this is then processed by an image structure identifier ID component.

The image identifier ID component uses a DD algorithm. As briefly described above, the difference image $V_A$ is processed to detect, by a suitable blob filter FD, a set of candidate locations each having a respective neighborhood. The neighborhoods of these candidate points are then analyzed by a feature analyzer FA, to extract from the candidate points the sub-set of location of interest LI's, preferably with the feature descriptors of their neighborhoods. The image co-ordinates of the LIs can be formatted into a feature map in Vm which can then be optionally displayed in a suitable grey value or color coding on the display unit by the operation of the visualizer VIZ. The map Vm is either displayed on its own or in combination with either one of the input imagery or other suitably registered imagery.

The identifier ID may be configured to classify the locations of interest LI into two, three or more classes according to the features in the respective neighborhoods as revealed in the feature descriptor step of the DD algorithm. The classification is according to feature strength in the descriptor and/or according to blob filter response magnitude in the detector stage of the DD algorithm. The (quantified) feature strength and/or the detector response magnitude are mapped by visualizer VIZ onto the grey or color palette to effect a graphical rendering of the neighborhoods around the LIs. However, graphical rendering of the location of interest with their neighborhoods is not envisaged in all embodiments, and in some embodiments a simple list view may be sufficient. In this list view, the co-ordinates of the locations of interest LI are listed alongside a numerical description of their features and the associated quantifications/strengths thereof. Preferably however, graphics display is generated for instance by fusion techniques in which the locations of the LI's are indicated preferably with a color coding of their respective neighborhoods in direct variance with feature strength. For instance, features that represent a strong likelihood or probability for bleeding can be indicated in one color (eg, red), whilst other neighborhoods are indicated in orange or green say to so indicate that these locations stand a lesser likelihood to represent a leakage situation than the red ones. This color combination is understood to be purely illustrative and other combinations are also envisaged herein. In one embodiment, color is used to visualize detector magnitude (class) whilst respective color hue is used to visually encode respective feature descriptor strengths within the given class. Other visualizations and combinations are also envisaged herein. These visualizations have been observed to be useful in user interactions.

The components of the image processing system IPS may be implemented as software modules or routines in a single software suit and run on a general purpose computing unit PU such as a workstation associated with the imager IA or a server computer associated with a group of imagers. Alternatively the components of the image processing system IPS may be arranged in a distributed architecture and connected in a suitable communication network. Alternatively some or all components may be arranged in hardware such as a suitably programmed FPGA (field-programmable-gate-array) or as one or more hardwired IC chips.

Figure 3:
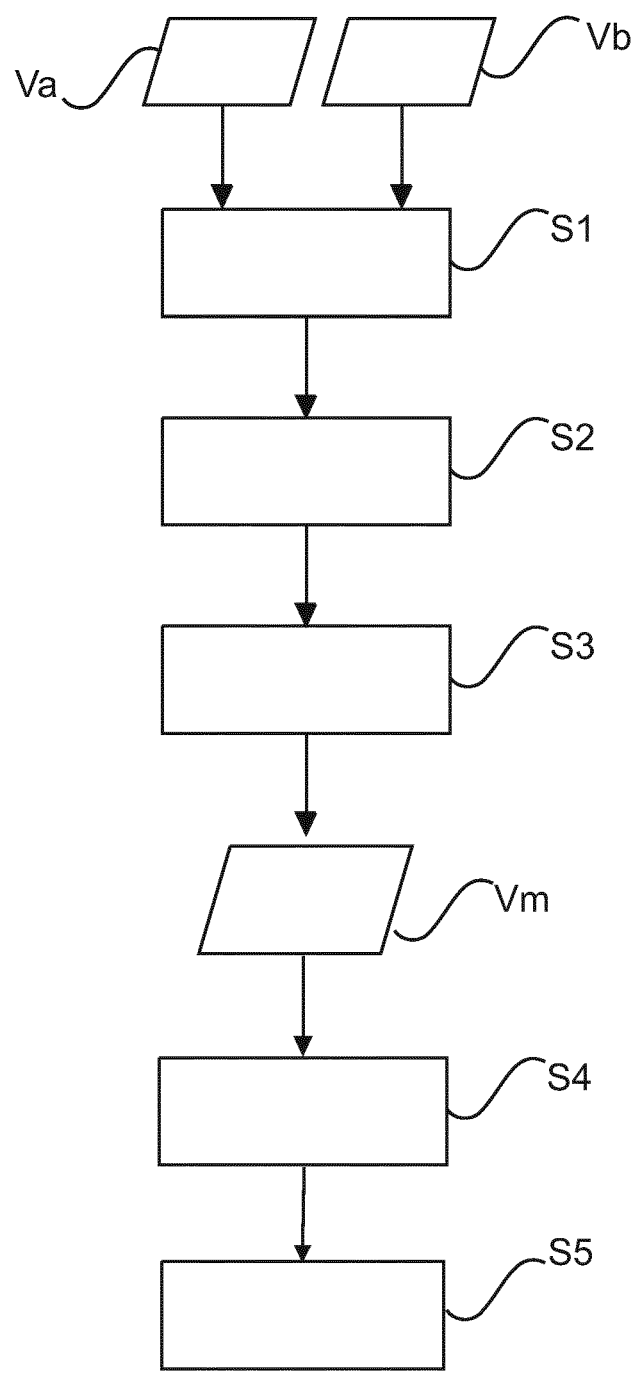
FIG. 3 shows a flow chart of a method of image processing.

Reference is now made to the flow chart in FIG. 3 that explains operation of the image processing system IPS in more detail. However, it will be understood that the following steps are not necessarily tied to the architecture as per FIG. 1. More particularly, the following described steps of the image processing may also be understood in its own right without reference to FIG. 1.

Commencing at step S1, the two input images, the earlier and the later VA, VB, acquired in the dual phased imaging protocol are received (not necessarily at the same time). The images are preferably directly supplied from the imaging modality (with or without suitable buffering). Alternatively, the images may be retrieved from (permanent) memory of a PACS, HIS or other memory/database system, upon request from a user or automatically via a protocol. Any suitable imaging modality is envisaged herein such as X-ray, CT, MRI, ultrasound and others. In the following, main reference will be made to dual phase X-ray imaging where the two (or more) images are acquired whilst a contract agent CA is present in the patient in the part of the body (eg, abdomen) that one wishes to image. The two images Va,Vb are hence capable of encoding the dynamics of the liquid of interest such as the blood flow. Instances of internal bleeding may still be difficult to find in these images by sole visual examination. To aid the user in this, the following steps are applied.

In step S2 the difference image $V_A$ is formed. The difference image is made up from difference image values. The difference image values may be obtained by taking pixel-wise (or voxel wise) arithmetic differences of the image values of the two input images. The difference image may thus include a distribution of positive and negative difference image values.

Preferably, a non-linear operation is applied in step S2 to the difference image values to obtain a weighted difference image. More particularly, the following steps may be performed in any combination or any selection thereof to construct the "two-phase" difference image, using non-linear functions or processing: first, one subtracts the first-phase image volume from the second-phase image volume (or vice versa). Then, difference values which are above a pre-determined first positive threshold are increased ("enhanced"). This increasing can be implemented by raising these difference values to a selected power (eg, to the power of 2 or according to any other power law) or by adding a suitable enhancement value or by multiplication with a suitable enhancement factor. This enhancement is done in order to give more weight to contrast material concentration in the second phase.

In addition to or instead so said enhancement operation, the non-linear processing of the difference values includes clipping of all or some of those difference image values, whose absolute value is above a determined second positive threshold, to said second threshold value. This clipping operation is done in order to suppress or regulate some overshoots of the image contrast due to previous enhancement.

In addition to, or instead of all the above enhancement and clipping operations, negative values in the difference image below a determined third negative threshold are clipped to said third threshold value. This is in order to suppress too high weights which may be given to very intense contrast material concentration in the first phase that can be present for example in normal blood vessels.

For ease of reference in the following we will refer to both the arithmetic difference image and the weighted difference image, simply as the "difference image $V_\Delta$" as the following steps are applicable to either embodiment. The thresholds used in this non-linear processing of the arithmetic difference image are related to the thresholds mentioned above on relation to the 5 properties i)-v) of the sign trading property whose presence has been found to be a good indicator for a leakage occurrence.

At step S3 one or more locations of interest LI are then identified in the difference image $V\Delta$. The so identified locations are indicative for leakage occurrences in the object.

Each location of interest LI are identified based on feature descriptors. The feature descriptors describe the respective neighborhoods (squares of circles in 2D or cubes or spheres in three dimensions or neighborhoods of any other geometrical shape).

The feature descriptors are configured to describe in particular intensity distributions of difference image values in the respective neighborhoods. As explained earlier the sign trading phenomenon observed to be at least partly characterizing in leakage situations will lead to neighborhoods that include regions with a relatively large positive values that are directly adjacent to those regions with relatively large negative values.

Preferably, but not necessarily in all embodiments, in order to make the analysis scale independent, the difference image is processed in a scale space representation such as pyramids or others. In other words, the difference image is processed by a series of filter operations to form down-sampled copies of the (original) difference image in progressively lower resolution. These copies can then be arranged in a hierarchy such as a Gaussian or Laplacian pyramid structure and it is this collection of copies which is being processed herein. Filters with a Gaussian kernel are preferably used. Such filters are aptly called Gaussian filters. The Gaussian kernel has the bell-shape of a Gaussian function. The Gaussian kernel (function), and hence the filter, can be described in particular by its standard deviation $\sigma$ (or variance $\sigma^2$). The standard deviation $\sigma$ is a measure of spread of the Gaussian kernel around a mean, which in turn describes the scale or amount by which the image is down-sampled. $\sigma$ can thus be used to parameterize each down-sampled copy of the difference image in the resolution pyramid.

The pyramid is said to be the scale space representation of the (original) difference image. This multi-scale representation of the difference image can be understood as an N+1 dimensional compound image. The original difference image is usually included into this compound image. The first N dimensions are the spatial dimensions of the respective down-sampled difference image or of the original, with N=2 or 3 (depending on the imaging modality), whilst the additional dimension is represented by the scale parameter $\sigma$ for the respective resolution level. For instance, a 2D difference image with spatial dimension coordinates x,y (or pixel location) will be represented in scale space representation with (x,y, $\sigma$) whilst for a CT image volume x,y,z (or voxel location) the scale space representation is in coordinates (x,y, z, $\sigma$). Scale space representation may instead be parameterized by the variance $\sigma^2$, or by any other suitable parameter in relation to the down-sampling operation.

The step of forming the difference image at step S2 and/or the DD algorithm based location identification in step S3 (to be described below) is/are preferably performed in said the scale space. In yet other words, the scale $\sigma$ co-ordinate of the scale space point will be considered as an (additional) "image" co-ordinate and the operations S2 and/or the following step S3 below are carried out across this additional dimension in addition to the analysis along the spatial image co-ordinate axes X,Y or X,Y,Z. Again, such multi-scale processing is, although preferable, not necessary, and embodiments are specifically envisaged where the processing steps are partly or entirely performed along the spatial dimensions only. "Mixed" embodiments are also envisaged where only a sub-set of the method steps are performed in scale space whilst other steps are performed along the spatial dimensions only. More generally still, in some embodiments, for a given step, only a sub-set of its sub-steps are performed in scale space with some (other) sub-step(s) are performed only in the spatial dimension.

One DD algorithm specifically envisaged herein in one embodiment has been found to be particularly advantageous for the proposed method of leakage detection. This algorithm of the DD type is commonly referred to as "SURF". It has been described by H Bay and others in a paper titled "Speeded-Up Robust Features (SURF)", published in Computer Vision and Image Understanding, Elsevier, vol 110, issue 3, 2008, pp 346-359. However, as mentioned earlier, other DD type algorithms are equally envisaged herein and the following description is of equal application to said other DD type algorithms. Such other DF type image processing algorithms include the Generalized Hough transform for detection of determined shapes, the "Histogram of oriented gradients" (or "HOG") feature descriptor. SURF is a variant of the "Scale-invariant feature transform" (or "SIFT") described by D G Lowe in *Distinctive Image Features from Scale-Invariant Keypoints, International Journal of Computer Vision*, Vol 60, Issue 2, November 2004, pp 91-110, likewise envisaged in some embodiments. Other DD type variants envisaged include the "Gradient location and orientation histogram" (or GLOH) approach and Harris-Laplace and Hessian-Laplace feature detectors or "Binary Robust Invariant Scalable Keypoints" (BRISK).

The SURF algorithm is advantageous because it allows very quick return and hence next to real-time experience of the visualization with image acquisition. This is made possible by using certain numerical techniques in the implementation of the SURF algorithm. In particular the Hessian blob detector is computed in approximation using integral images. The approximation can then be computed advantageously with only three arithmetic operations using the pre-computed integral images retrievable in only 4 memory access operations. "Real time" as used herein refers to the user experience relative to the image acquisition and/or the time when the images are received for processing at step S1. The indication of the leakage can then be produced quasi-instantaneously which is of particular advantage in frontline operations, such as onsite interventions, in ambulance vehicles or in emergency rooms. To increase the real-time quality, all or a part of the method steps may be/performed by specialized processors, such GPUs (graphical processing units) instead or in support of more conventional processor types. That is not to say however that non-real time implementations are excluded herein. These slower implementations of the proposed method may still be used, for instance when analyzing historic image data retrieved from storage system for training or teaching purposes.

In general, image processing algorithms of the DD type are designed to analyze a 2D image or 3D image-volume and to spatially indicate interest-points where the image region in the neighborhood of such point has desired morphological and image value distribution features. The analysis locates the relevant points in the analyzed space (preferably scale space) and quantifies, using mathematical descriptors, the strength of desired features.

During the analysis, a set of filter kernels are applied to each pixel or voxel neighborhood in the analyzed space and the filter response is calculated (e.g., by a convolution function). The filter kernels are usually based on Gaussian functions, their derivatives or combinations of them, on weighted region masks or on various wavelets functions.

Preferably, this analysis is configured to be rotation and/or orientation invariant and/or scale invariant. The purpose of such invariances is to be able to extract fundamental morphological features of an image region independently of the region size and the overall orientation of the structures.

Preferably, a non-maximum suppression operation is used in the extraction which allows reducing the set of possible candidate points, as otherwise a very large set is returned. In other words, the non-maximum suppression results in a limited set of the most important interest-points. Specifically, the non-maximum suppression allows isolating a candidate points having the strongest set of features among other possible point candidates in close proximity. Proximity may be measured in spatial dimensions only or, preferably, in scale-space.

Since the analysis is performed across different scales and morphology structure types, e.g. by using filter kernels of different sizes, and by using kernels of different shapes, the detected interest-points can be sub-classified based on pre-determined properties. For example, one may discriminate between points which have stronger response to different filter kernel shapes, or stronger response to kernels in different sizes, etc.

In image algorithms of the DD type as envisaged herein, the purpose is to extract robust and general features such as those based on corners and edges of shapes, and on differences between salient regions or blobs. Usually, there is no attempt to detect too specific geometrical shapes since the analysis will lose its generality and practicality. The DD type approach has been found to be well suited for the clinical problem of leakage detection since the mentioned interest-points in the difference image can have the sign trading property, without having very specific geometrical shapes or sizes. In other words, the sign trading property can still be detected, despite its manifestation in the difference image in different geometrical shapes or shape distributions.

In general terms, the identification step S3 (for the identification of the location of interest) includes broadly the following: in the first step the DD algorithm is applied to the difference image. This yields the candidate locations with their respective descriptors. As mentioned earlier, the DD algorithm includes the detection operation. The detector operation is carried out with a detection filter such as a blob filter. The detection filter will elicit a response at different image locations. Depending on the strength of the response, a classification of the candidate points can be carried out. This allows then outputting the locations of interest classified or ranked according to the strength of the detector response. In addition or alternatively, the feature descriptor strength may also be used for classification.

Describing now in more detail the DD algorithm application in step S3, the DD algorithm will be explained with particular reference to the SURF algorithm with the understanding that this is just one embodiment of the proposed method and other algorithms than SURF can be applied to implement the identification step S3.

The SURF algorithm (and similar ones derived from or otherwise related to SURF) can be described in general in four sub-steps. First, the interest point detector is applied to the difference image. The detection of interest points is done using Hessian-matrix analysis based on three filter kernels, which are approximations to the second derivatives in the directions (XX, YY, XY). The filters are applied using different kernel sizes, to analyze different scales across scale space representation of the difference image.

The second sub-step is the localization of candidate interest points in the difference image by applying non-maximum suppression, with regard to the maxima of the determinant of the Hessian-matrix. This process may also include interpolations in scale and image space. The result of this sub-step is a group of candidate interest points in the difference image, each one being specified by its spatial coordinate and its dominant scale $\sigma$.

In the third sub-step, the dominant orientation (i.e. an angle in the spatial dimensions X,Y of image space) of the interest point is found by applying Haar-wavelet filter analysis both, in X and Y directions in respective neighborhoods of the candidate interest points. The purpose is to select a dominant orientation for which the image gradients are more pronounced in the relevant neighborhood.

The fourth sub-step provides more detailed and robust mathematical descriptors of the properties of each interest point and/or its neighborhood. A neighborhood suitably defined in size and shape (eg, square, circular or other) is centered on the candidate interest point and oriented along the dominant orientation, with neighborhood size being a function of the dominant scale $\sigma$ of the candidate interest point.

The neighborhood may be divided into sub-regions (e.g. 4×4 squares, but this is exemplary and not limiting). Each of the sub regions is analyzed with X' and Y' Haar-wavelet filters (where X' and Y' are now spatial directions relative to the dominant orientation of the interest point) and one of or both the signed and absolute response values in each direction is calculated. Overall then, the candidate interest points are described by a respective descriptor vector including all of the last calculated responses. In the above noted example for the 4×4 sub-division of the neighborhoods, the respective vector has 64 elements, but, again, this is merely for illustrative purposes and not limiting.

The vector entries are quantifications (numbers) of suitable image features that singly or in combination describe characteristics of the distribution of positive and negative difference image values in the respective neighborhoods. The feature quantifications have magnitude so can be said to represent a "strength" of each feature as listed in the description vector. The localization step S3 as proposed herein envisages in one embodiment to use several different Hessian-response thresholds (e.g. two, three or more) for the interest point detector (such as the Hessian matrix analysis) approach in SURF. The different thresholds allow classifying between different interest point classes.

Although the analysis can be directly applied in 3D using 3D wavelets, it may also be applied instead by using 2D wavelets across 2 or more 2D cross-section slice images of the 3D difference image. This allows extending the SURF technique or other DD type algorithm from a previously single image approach to a multiple image approach where this plurality of 2D cross sectional images is separately analyzed. For instance, the set of images to be analyzed in step S3 may be chosen in one embodiment as all slices of the volume along all three perpendicular views, such as trans-axial, coronal and sagittal directions. The analysis is then applied to each of these 2D images. In his way the 3D volume can be analyzed in a near-isotropic manner. The advantage is that the analysis still takes place in 3D but only 2D wavelets are used instead of 3D wavelets, the latter being computationally more expensive.

For each of the class thresholds, the SURF analysis as described above is applied to each selected image in turn.

For each detected candidate interest-point in the difference image (or slice image there through), the scale σ, a polarity of the neighborhood, and the maximum of the descriptor vector will be extracted. The polarity (e.g. −1 or 1) is found by a Laplacian analysis of the interest-point neighborhood. In the current usage, only those candidate points will be selected as a location of interest LI whose feature polarity is related to a leakage event. For instance, a polarity=1 has been found to be so related. As used herein, "polarity" refers to a mathematical description of the direction or the mathematical sign (+ or −) of the specific analysis of the local image feature. In one embodiment, the polarity analysis uses the Laplacian operator which is based on the second derivatives. In the difference image, neighborhoods having the sign trading property will have, on average, positive second derivatives. Hence, only candidate locations with neighborhoods having "positive" Laplacian will be considered. In other formulations, negative polarity is preferred. This is in particular so if the difference image is formed the other way around, that is by subtracting the second phase image from the first phase image.

The selection from the group of candidate points may instead or in addition be based on a weighted average across some or all descriptor vector entries. The features considered may be confined to the spatial dimensions but may instead include the scale dimension σ.

According to one embodiment, the candidate interest points are adopted as locations of interest, if their respective polarity is in the desired sign and the scale is within a determined range, determined against a pre-determined set of scale thresholds. If the candidate point is so adopted, the respective feature weight or strength is taken as the value of the maximum of the feature descriptor vector or, as mentioned, as a weighted average of features across the vector.

If several classification thresholds are used, the above described SURF analysis or any other DD type algorithm can be implemented in a sequential fashion as follows: first perform the analysis as described above using the highest threshold value. The result of the analysis will provide the group of the most dominant class of candidate interest points. Next, repeat the whole analysis while setting the next (lower) value of the detector threshold. The detected interest points will include the former points from the first step plus some new points. The new points will be assigned to the second class of interest points. The process is repeated again, with all determined classification thresholds taken in turn. After each repetition the new detected points are grouped into a new class.

Since the analysis is applied volumetrically, an averaging or an additional non-maximum suppression is applied to the difference volume in order to reduce the set of locations of interest to so avoid or mitigate "bunching up" or overlapping of locations of interest. For example, in a certain small volumetric region the most significant point between the three views (trans-axial, coronal and sagittal) will be selected for constructing the visualization for this region.

In all of the above, the various thresholds used can be set once empirically using true or simulated test cases analyzed by a person, or by applying machine-learning techniques to find the best parameters using a set of true imagery representing real or simulated leakage events.

The described analysis will provide "high response" precisely at image structure having the sign trading property since this kind of structure will give high response to a convolution with Haar wavelets, both in the X and Y directions. The response will be maximized only for the correct wavelets with the appropriate scale (size) and with the correct direction (angle in the 3D volumetric coordinates) if the shape of the sign trading structure is not circular symmetric.

In sum, the proposed method will generate high response in the desired sign trading structure, both by properly constructing the difference image and by correctly selecting the appropriate wavelets for the convolution. The preferred scale and direction of the wavelets are effectively determined in 3D (by analyzing all three orthogonal views) thus extending the SURF technique from single image or a multi-image processing.

At the conclusion of the identifying step S3, the locations of interest LI so identified together with their feature strength descriptors form a feature map which can then be used to inform the user about possible leakage locations in either one of the input images VA or VB.

At step S4 the feature map(s) are output and made available for further processing of storage or are used otherwise.

Preferably, but not necessarily in all embodiments, the feature map Vm is visualized in step S5 on a display unit DU.

In one embodiment, graphical representations of the respective neighborhoods are rendered for display at the locations of interest. This may be done by color coding said neighborhoods according to their class and/or the strength of their feature descriptor vector. For instance, the class may be color-coded whilst feature strength is coded as modulation of hue for the respective class color. Fusion rendering techniques are used in one embodiment to fuse the feature map with the input imagery (that is, the earlier or later image Va, Vb) or with other imagery registered to the input imagery.

It will be understood that in the embodiment where a classification according to different detector responses are performed, one obtains as output at step S3 a plurality of such feature maps, one for each class.

Specifically, and according to one visualization embodiment, a dedicated color scheme is assigned to each morphological class. The color scheme level or hue is based on the calculated feature weight. The color values of the whole class volumes are then combined into a single colored volume.

Figure 4:
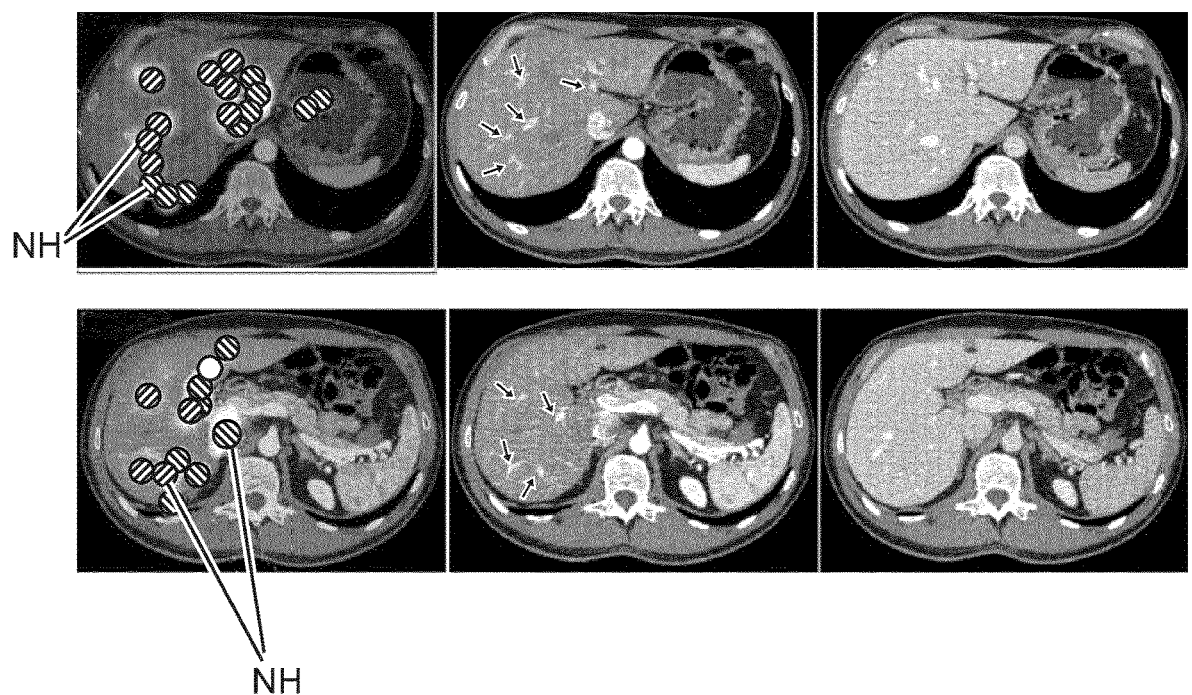
FIG. 4 shows a visualization of a feature map obtainable by the method of FIG. 3.

FIG. 4 is a schematic representation of a feature map visualization with neighborhoods NH rendered as circles in the first column. The upper and lower row show different slice images taken at different positions through a CT image volume. The possible leakage locations are shown using arrows in the middle column. The middle column represents the early phase image and the right hand column the delayed phase imagery.

Optionally, a floating scheme may be used by overlaying higher-importance classes "on top" of classes of lesser importance. Image fusion (or blending) of the colored feature significance map with a CT image volume may then be used as shown in FIG. 4.

The two slice-position examples in FIG. 4 shows a feature-significance probability distribution of the detected interest regions which are associated with the described effect typical for leakage events. In the exemplary embodiment of FIG. 4, three morphological classes are shown, with three different color schemes. The intensity (ie, the probability) in each color scheme is visualized by adding hue to a base color and by color-coding the feature weights in the image fusion blending.

It is of note that many regions that are well enhanced in the early phase but less enhanced in the later phase (such as the aorta and the normal spleen) are not detected, which is intended.

In one embodiment, the feature map Vm may be normalized so as to represent a graphical representation for leakage probabilities. Specifically, after obtaining at step S3 the (initial) feature-significance map VM, a volumetric probability distribution map can be constructed from this initial map which may be more adequate for visualization in a clinical workflow. To construct the probability map, a volumetric smoothing kernel, for example a 3D Gaussian kernel, is applied to the initial map or volume where the interest point voxels are set to '1.0' and all the other voxels to '0.0' to so achieve the normalization. This can be applied separately to the volume of each morphological class. The visualization of these results can be realized in several image fusion blending techniques, such as shown in FIG. 4.

As a further visualization option, a user may interactively set and adjust the feature-significance map visualization and may show less or more morphological classes, with a link to pictorial examples. This can be also executed in real-time during clinical reviewing of the case. As additional option, spectral CT iodine-maps can be used for the processed subtraction image.

The imagery used in FIG. 4 represents a test case. No actual bleeding is shown but the proposed method is applied to anatomies that mimic bleeding events. Specifically, the imagery in FIG. 4 is drawn from dual-phase contrast CT including the arterial and portal phases of the liver. The liver includes regions which mimic very well active bleeding as mentioned above. Overall, this demonstration shows very good identification of the leakage events or processes that produce similar image effects. Of course, as mentioned above, from a clinical point of view, such healthy regions in the liver represent false-positive detections by the proposed method. However, the proposed method is intended to support faster and easier reviewing of other suspicious regions such as the spleen or the space between abdomen organs which normally will not show such behavior. The user should thus ignore false positive detection in anatomies which are a priori know to exhibit normal activity that merely produce imager effects akin to a leakage situation. To mitigate such false-positive responses, organ segmentation priors may be used.

Although the method has been described with main reference to 3D imagery such as CT image, application to more conventional 2D radiographs or other 2D imagery is also envisaged herein, and so is imagery acquired by modalities other than X-ray, such as MRI, PET/SPECT, US or others.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
an input interface for receiving an earlier input image and a later input image acquired of an object whilst a fluid is present within the object, wherein said object is a human or animal anatomy and said liquid is blood, and wherein the earlier input image and the later input image have been acquired after injection of a contrast agent;
a differentiator configured to form a difference image from the at least two input images;
an image structure identifier operable to identify in the difference image one or more locations of internal bleedings, where blood escapes through a leakage point in a vessel, based on a respective feature descriptor computed to describe a respective neighborhood around said one or more locations, if a region, in the difference image with negative values is adjacent to a region, with positive values; and
an output interface for outputting a feature map that includes the one or more locations.

2. The image processing system of claim 1, wherein the forming by the differentiator of image values of the difference image includes taking differences to obtain difference image values and increasing or decreasing said difference image values based on one or more pre-set intensity thresholds to obtain adjusted difference image values.

3. The image processing system of claim 1, wherein said feature descriptor is computed by the identifier to describe an intensity distribution in said neighborhood.

4. The image processing system of claim 3, wherein the intensity distribution is indicative of blood escaping through the leakage point in the vessel within the human or animal anatomy.

5. The image processing system of claim 1, wherein the identifier is configured to compute the feature descriptor based on a wavelet analysis of the difference image.

6. The image processing system of claim 5, wherein the wavelet analysis is applied along different spatial directions.

7. The image processing system of claim 1, wherein the one or more locations of interest are identified from among a collection of candidate locations computed by a feature detector applied to the difference image.

8. The image processing system of claim 1, comprising a visualizer configured to render on a display a visualization of said feature map in spatial association with at least one of the input images or with another image of the human or animal anatomy.

9. The image processing system of claim 8, wherein the visualization includes a representation of the respective neighborhood, said representation being color- or grey value coded based on a strength of the respective feature descriptor or on a strength of a response of the feature detector.

10. The image processing system of claim 9, where at least one of the input images is any one of: a CT image, an MRI image, a US image, a PET or a SPECT images.

11. A method of image processing, comprising:
receiving an earlier input image and a later input image acquired of an object whilst a fluid is present within the object, wherein said object is a human or animal anatomy and said liquid is blood, and wherein the earlier input image and the later input image have been acquired after injection of a contrast agent;
forming a difference image from the at least two input images;
identifying in the difference image one or more locations of internal bleedings, where blood escapes through a leakage point in a vessel, based on a respective feature descriptor computed to describe a respective neighborhood around said one or more locations, if a region, in the difference image with negative values is adjacent to a region, with positive values; and
outputting a feature map that includes the one or more locations.

12. A non-transitory computer readable medium having one or more executable instructions stored thereon, which, when executed by processor circuitry, cause the processor circuitry to perform a computer implemented method of image processing, the method comprising:
receiving an earlier input image and a later input image acquired of an object whilst a fluid is present within the object, wherein said object is a human or animal anatomy and said liquid is blood, and wherein the earlier input image and the later input image have been acquired after injection of a contrast;
forming a difference image from the at least two input images;
identifying in the difference image one or more locations of internal bleedings, where blood escapes through a leakage point in a vessel, based on a respective feature descriptor computed to describe a respective neighborhood around said one or more locations, if a region, in the difference image with negative values is adjacent to a region, with positive values; and
outputting a feature map that includes the one or more location.

13. The image processing system of claim 7, wherein the one or more locations of interest are identified from among the collection of candidate locations computed by the feature detector applied to the difference image in a scale space representation of the difference image.

* * * * *